(12) United States Patent
Steiner et al.

(10) Patent No.: US 8,486,074 B2
(45) Date of Patent: *Jul. 16, 2013

(54) SURGICAL ALLOGRAFT BONE PLUG CUTTING TOOL ASSEMBLY AND METHOD OF USING SAME

(75) Inventors: Anton J. Steiner, Warton, NJ (US); David I. Knight, Perth Amboy, NJ (US); Paul J. Mulhauser, New York, NY (US); Karl D. Kirk, III, New York, NY (US); Richard J. Cosenza, Island Park, NY (US); Gregory C. Fanelli, Danville, PA (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 592 days.

This patent is subject to a terminal disclaimer.

(21) Appl. No.: 12/457,098

(22) Filed: Jun. 1, 2009

(65) Prior Publication Data

US 2009/0299372 A1 Dec. 3, 2009

Related U.S. Application Data

(60) Provisional application No. 61/129,055, filed on Jun. 2, 2008.

(51) Int. Cl.
*A61B 17/00* (2006.01)
(52) U.S. Cl.
USPC ............................................. 606/79
(58) Field of Classification Search
USPC ............ 606/79–80, 86 R, 174; 144/345, 144/355, 375
See application file for complete search history.

(56) References Cited

U.S. PATENT DOCUMENTS

| | | | | |
|---|---|---|---|---|
| 2,196,701 A | * | 4/1940 | Homsher | 408/227 |
| 5,759,185 A | * | 6/1998 | Grinberg | 606/80 |
| 5,919,196 A | | 7/1999 | Bobic et al. | |
| 5,954,671 A | * | 9/1999 | O'Neill | 600/567 |
| 5,993,453 A | * | 11/1999 | Bullara et al. | 606/79 |
| 6,488,033 B1 | | 12/2002 | Cerundulo | |
| 6,591,581 B2 | | 7/2003 | Schmieding | |
| 6,592,588 B1 | | 7/2003 | Bobic et al. | |
| 6,852,114 B2 | * | 2/2005 | Cerundulo | 606/80 |
| 7,780,668 B2 | * | 8/2010 | Steiner et al. | 606/79 |
| 7,959,636 B2 | * | 6/2011 | Schmieding | 606/86 R |
| 2004/0034437 A1 | * | 2/2004 | Schmieding | 623/908 |
| 2005/0106531 A1 | * | 5/2005 | Tang | 433/76 |
| 2006/0293679 A1 | * | 12/2006 | Buttler et al. | 606/86 |
| 2008/0255623 A1 | * | 10/2008 | Steiner et al. | 606/86 R |

* cited by examiner

*Primary Examiner* — Andrew Yang
*Assistant Examiner* — Diana S Jones
(74) *Attorney, Agent, or Firm* — John S. Hale; Gipple & Hale

(57) ABSTRACT

The invention is directed toward a surgical kit having component parts capable of use to prepare a cartilage implant plug from allograft condyle. The kit comprises a sizing gauge used to measure surface of the allograft condyle so that a cartilage implant plug can be removed that corresponds to the contours of the defect site excised on a patient. An adjustable guide member is mounted in a fixed orientation over the allograft condyle in which a cylindrical graft cutter for cutting a cylindrical allograft bone plug having a cartilage cap and a bone end portion. A chamfering tool is used for chamfering the bone end of the allograft bone plug.

6 Claims, 14 Drawing Sheets

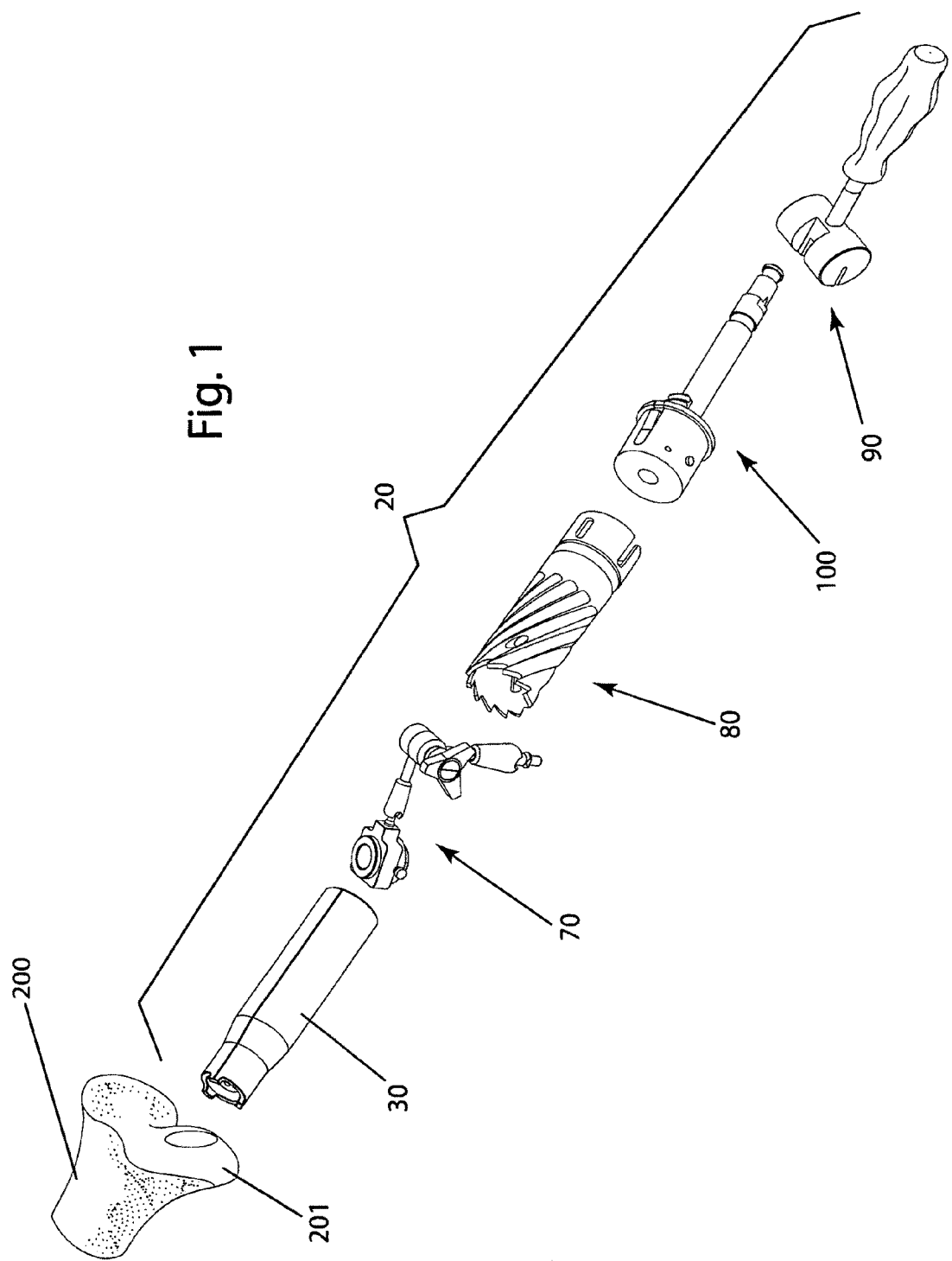

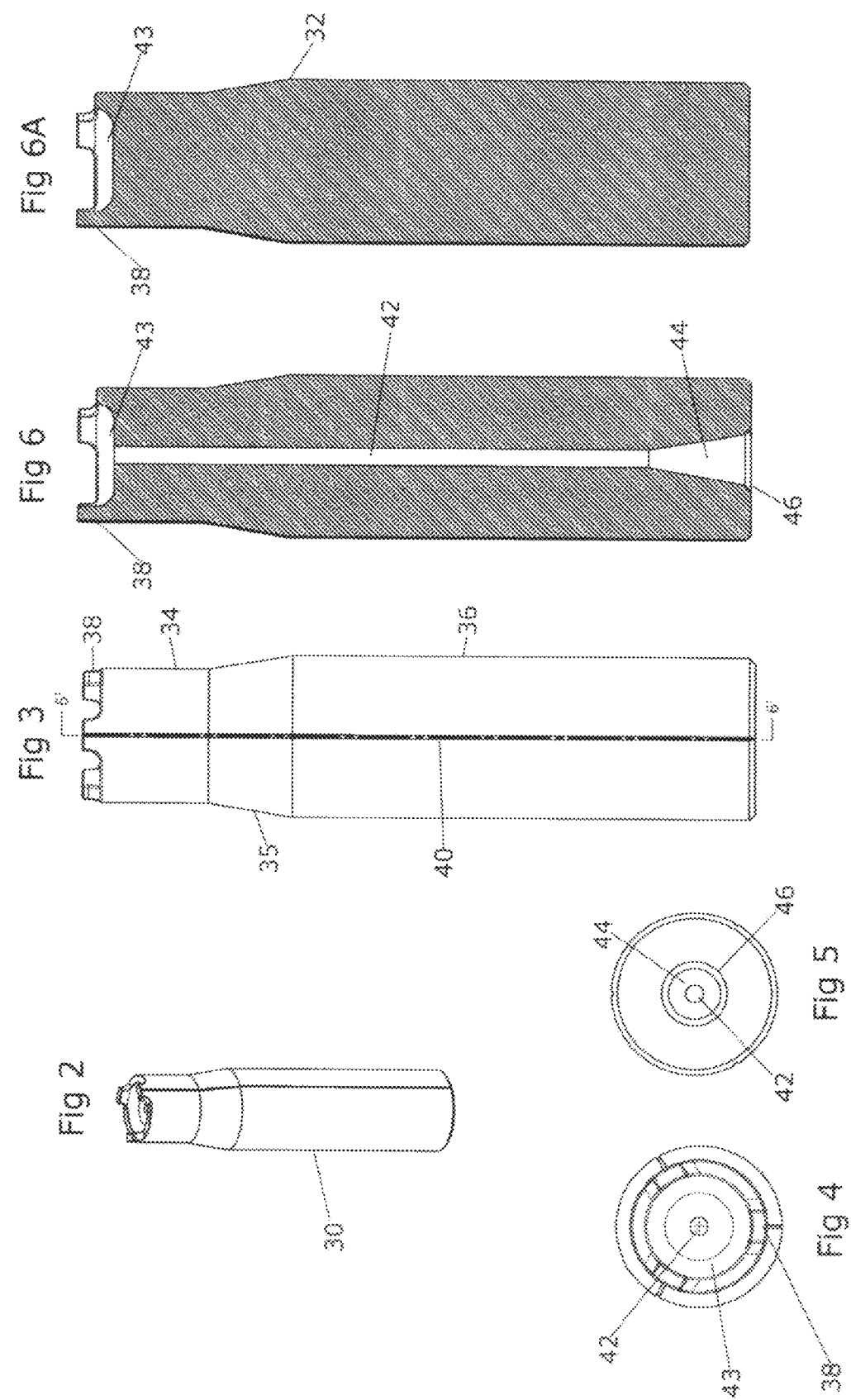

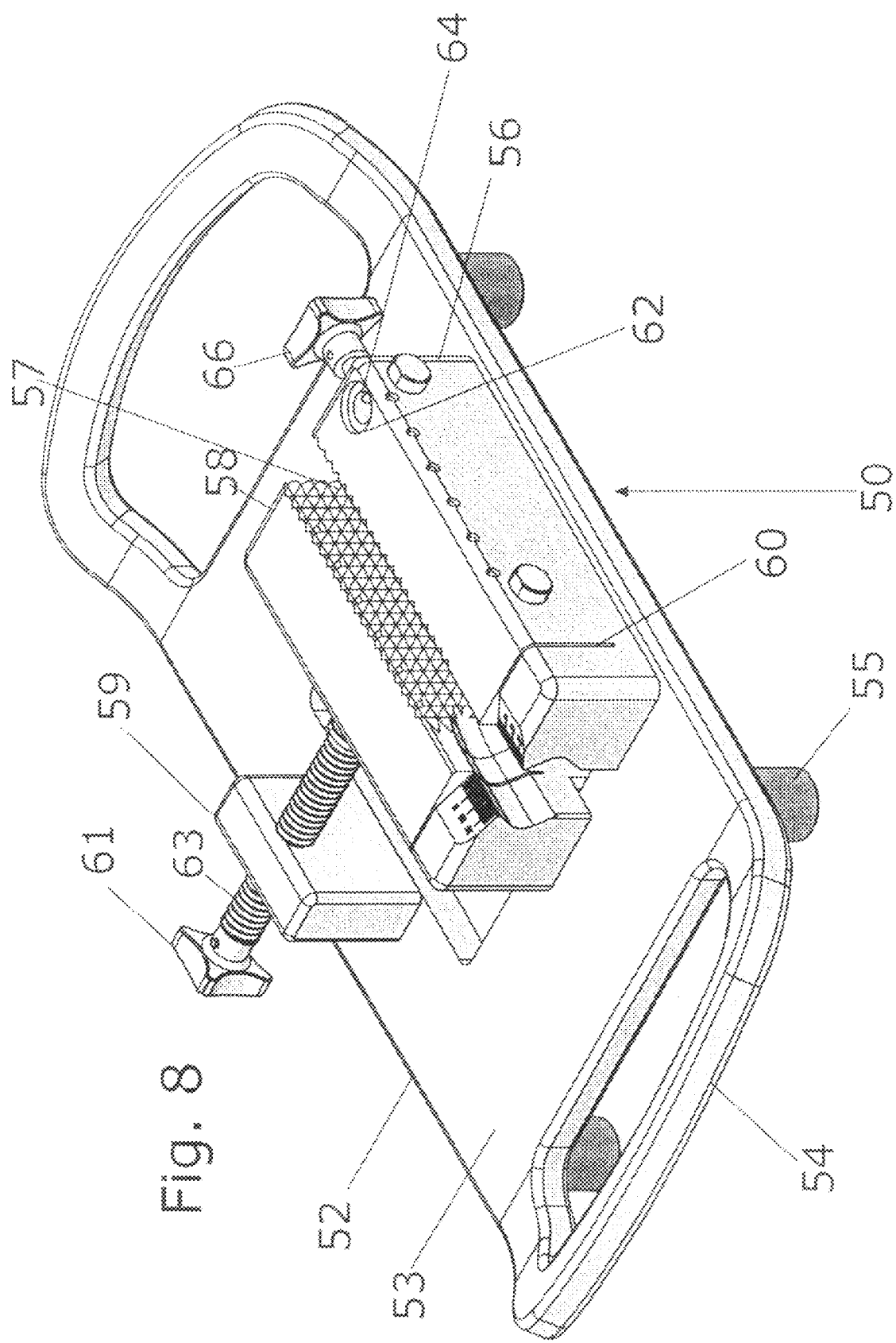

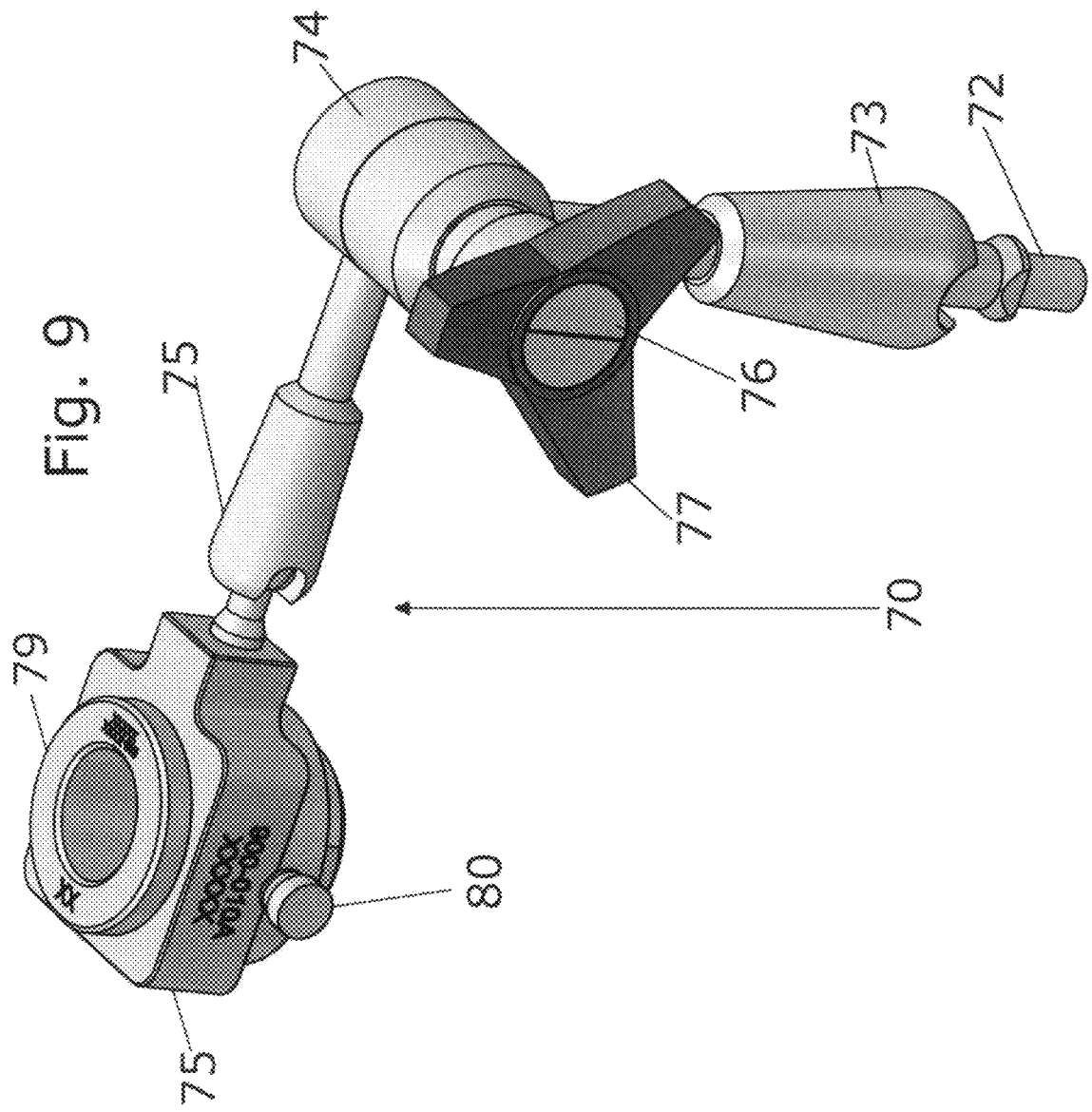

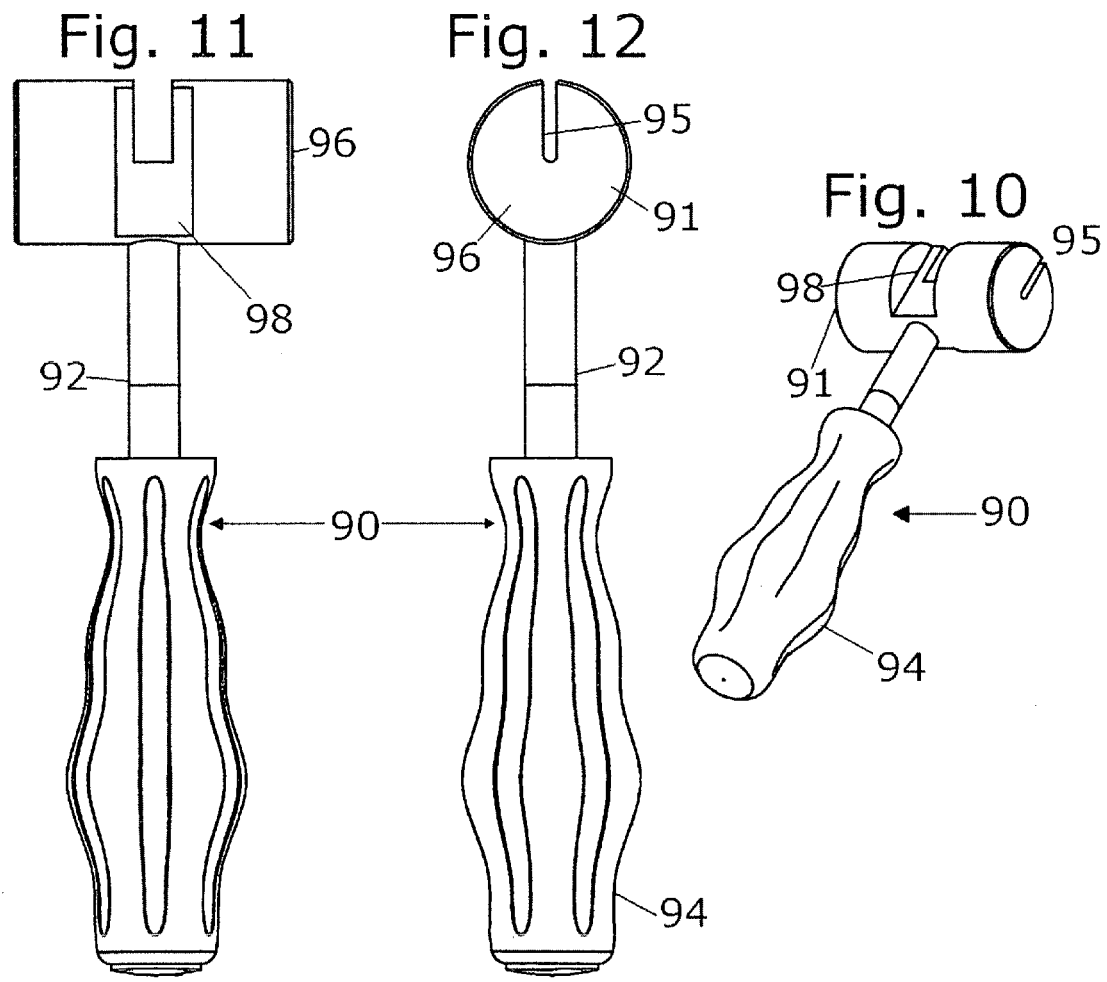

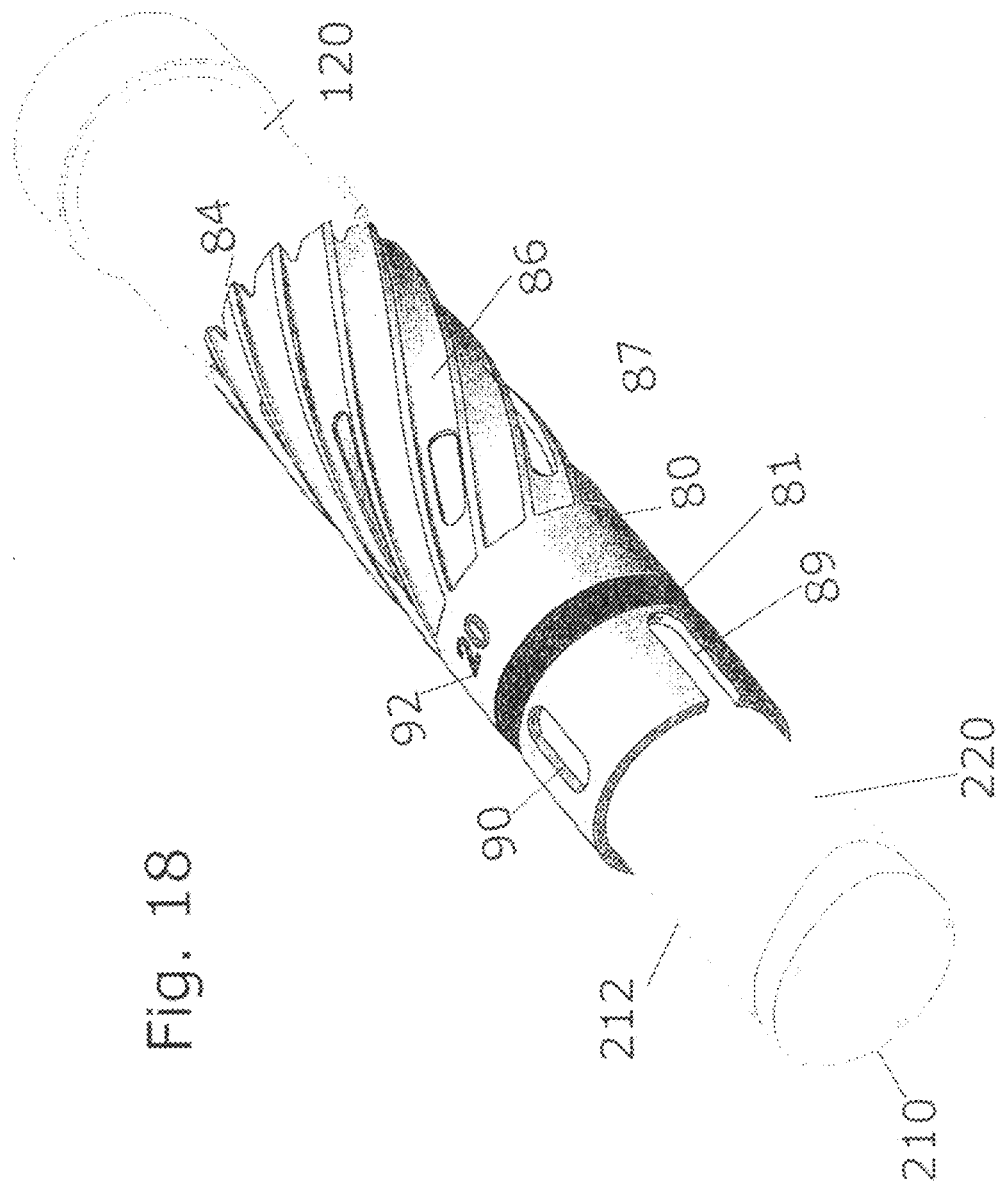

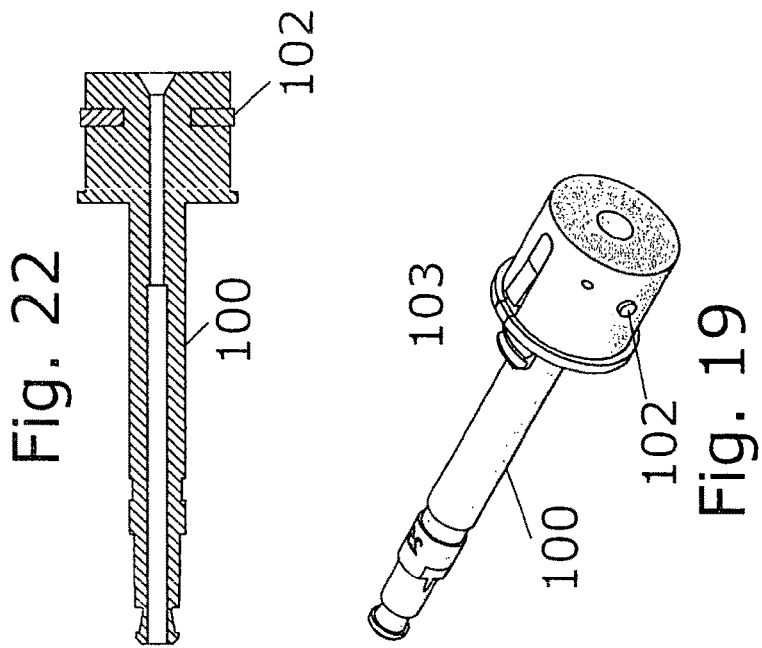
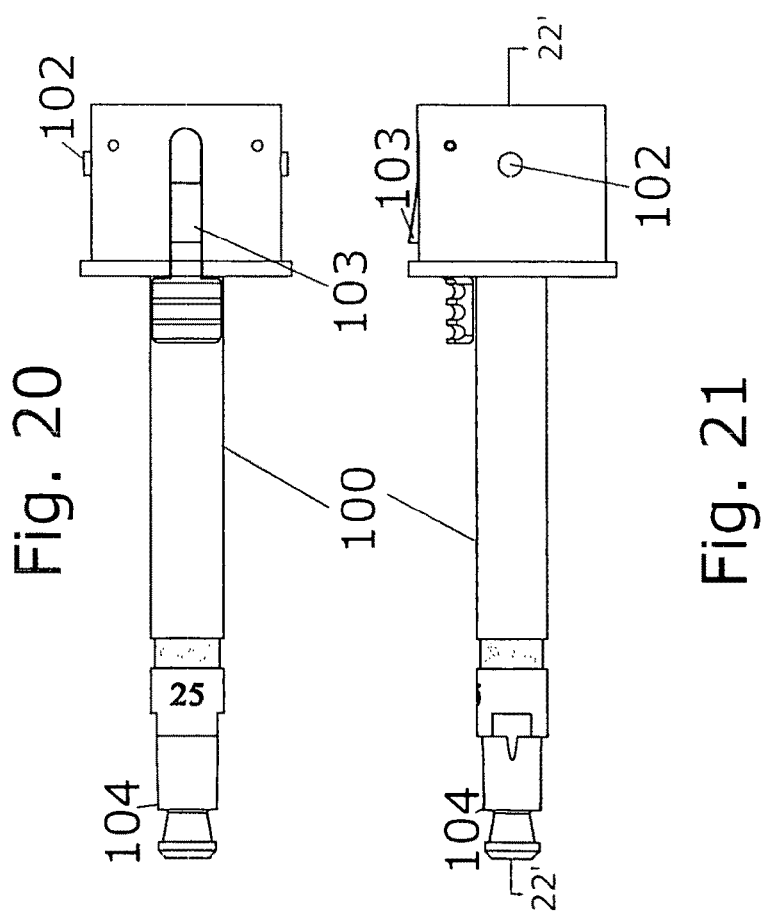

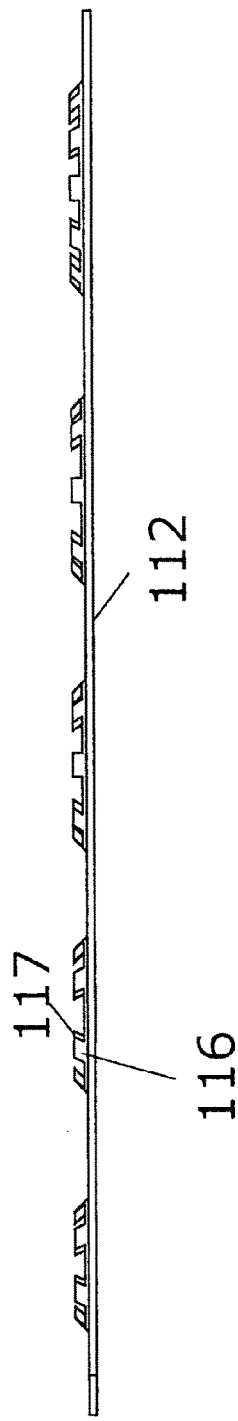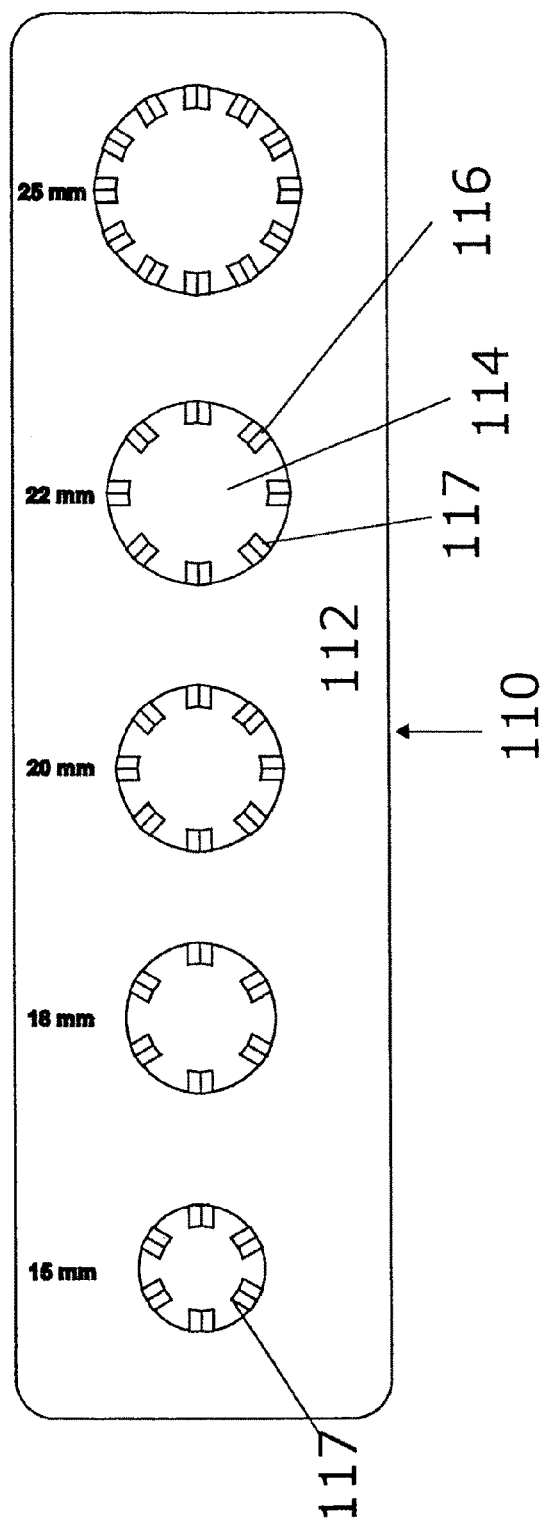

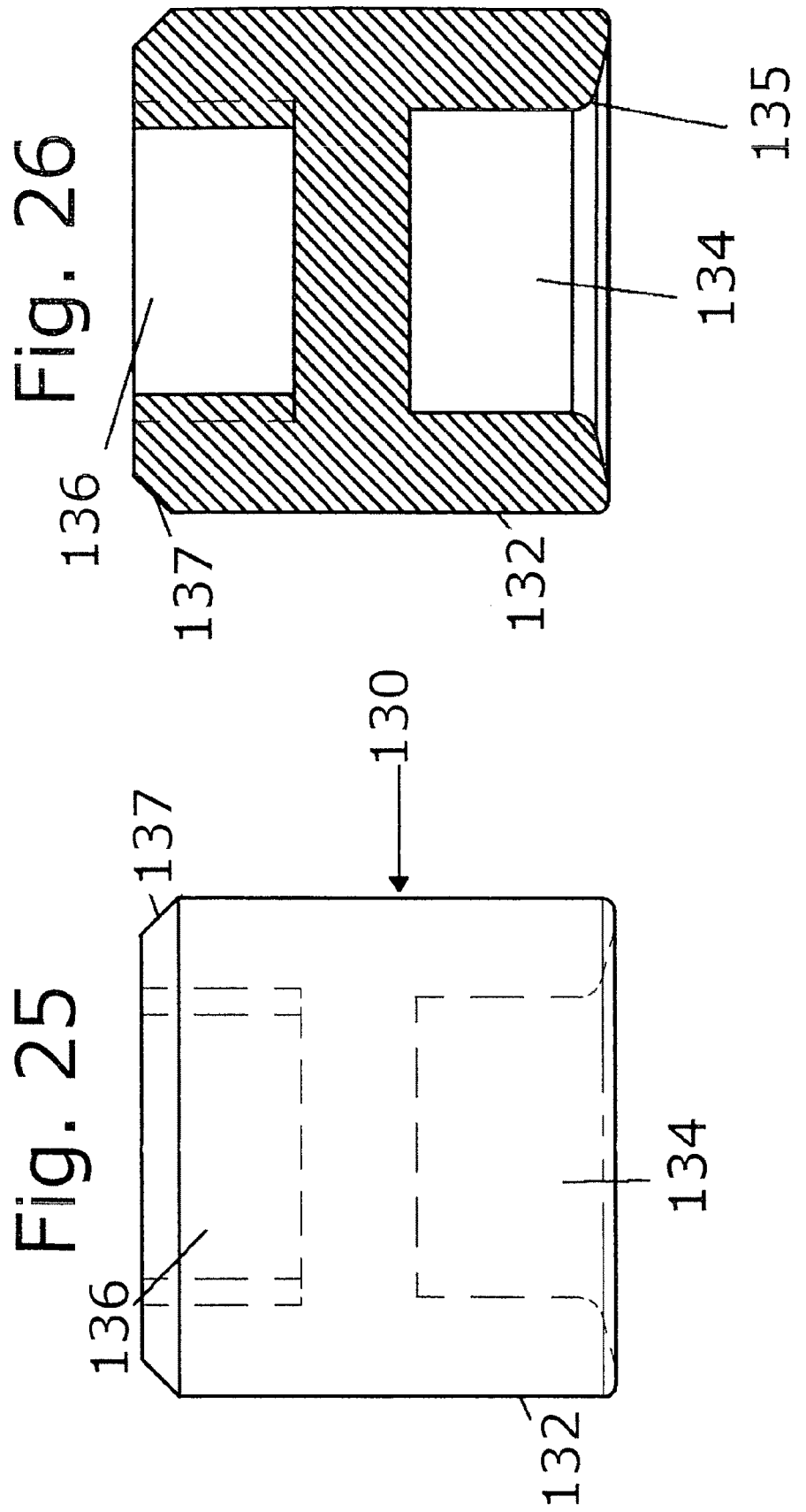

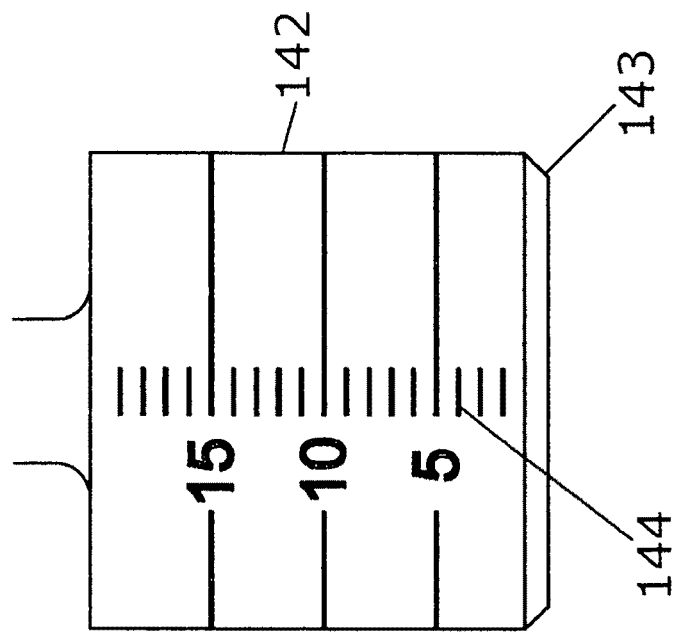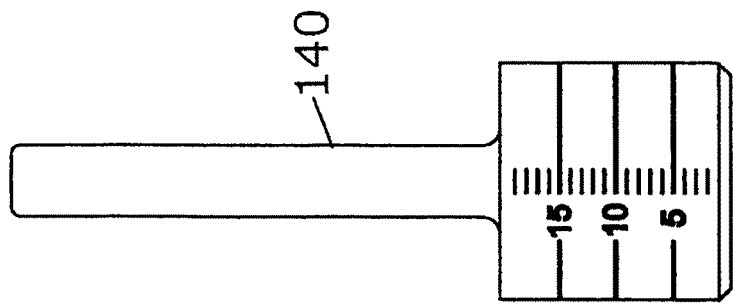

SURGICAL ALLOGRAFT BONE PLUG CUTTING TOOL ASSEMBLY AND METHOD OF USING SAME

RELATED APPLICATIONS

The present application is related to and claims priority from U.S. Provisional Patent Application No. 61/129,055 filed Jun. 2, 2009.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention is generally directed toward the surgical treatment of articular chondral defects and is more specifically directed toward a surgical cutting tool assembly for repairing a cartilage defect of a patient by cutting a cylindrical allograft cartilage implant plug from a condyle for orientation and placement in a blind bore cut in a patient.

2. Description of the Prior Art

Articular cartilage injury and degeneration present medical problems to the general population which are constantly addressed by orthopedic surgeons. Every year in the United States, over 500,000 arthroplastic or joint repair procedures are performed. These include approximately 125,000 total hip and 150,000 total knee arthroplastics and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of an extracellular matrix with a sparse population of chondrocytes distributed throughout the tissue. Articular cartilage is composed of chondrocytes, type II collagen fibril meshwork, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint. If the cartilage lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of nerves, blood vessels and a lymphatic system. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time.

Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. Patient or recipient repair sites are normally present in the weight bearing area of the medial and lateral femoral condyles. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age have obtained good clinical results, which most likely reflects the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. CARTICEL® is a commercial process to culture a patient's own cartilage cells for use in the repair of cartilage defects in the femoral condyle and is marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks. Once cultivated, the cells are injected during a more open and extensive knee procedure into areas of defective cartilage where it is hoped that they will facilitate the repair of damaged tissue. An autologous periosteal flap with cambium layer is sutured around the defect and is used to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and that biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The autologous osteochondral plugs are harvested from a lower weight-bearing area of lesser importance in the same joint. Reports of results of osteochondral plug autografts in a small numbers of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts also carry the risk of immune response or disease transmission. Musculoskeletal Transplant Foundation (MTF) has preserved fresh allografts in a media that maintains a cell viability of 50% for 35 days for use as implants. Frozen allografts lack cell viability and have shown a decreased amount of proteoglycan content which contribute to deterioration of the tissue.

A number of United States patents have been specifically directed towards the manufacture of plugs or cores which are implanted into a cartilage defect. U.S. Pat. No. 6,591,581 issued Jul. 15, 2003 describes a precut bone plug for use in allograft core transplantation surgery in which a tissue bank harvests the graft using a coring trephine with teeth having an inner diameter between 0.5 mm to 0.1 to create a bone core with a hyaline cartilage layer of approximately 7.9 mm, 9.9 mm, 11.9 mm diameters. A donor cutting harvester having a cutter tube with a straight cutting edge, a window slot and depth markings with a torque handle on the proximal end may be used to obtain an autograft core as is shown in U.S. Pat. No. 5,919,196 issued Jul. 6, 1999. This same reference also discloses a punch cutter which is cannular. As noted in U.S. Pat. No. 6,591,581 issued Jul. 15, 2003 an allograft osteochondral transplantation method is known, in which a surgeon is provided with a whole cadaver knee from a tissue bank along with an instrument set containing the full range of sizers and sized instruments. In this allograft method, the surgeon must determine the size for the graft needed and then perform the surgery. The '581 patent notes that this method is undesirable due to several factors including the preoperative preparation required for the surgeon to harvest and prepare the donor core, the waste from discarding each cadaver knee after the one operation without realizing the full potential for each knee to yield multiple allograft cores and the comprehensive instrumentation system which must be sent to and recovered from the operation site. This patent discloses instruments for cutting a bone core by cutting or punching having collared pins disposed within the harvester for removal of the harvester cores. U.S. Pat. No. 6,592,588 issued Jul. 15, 2003 discloses apparatus for allograft transplantation of articular cartilage with bone from one site to another to treat chondral defects. The '588 patent discloses a handle having a cylindrical bar extending through it transverse to the axis of the cutting tube mounted to the handle. The cutting tube is provided with a longitudinal slot which allows view of the depth of the penetration of the cutting tube.

U.S. Pat. Nos. 6,488,033 and 6,852,114 (a divisional application of the '033 patent) issued respectively Dec. 3, 2002 and Feb. 8, 2005 are directed toward an osteochondral transplant workstation for cutting a core out of an allograft bone held in an adjustable vise with a lubricated rotary cutting bit. The core is removed from the bit, held in a specially designed set of pliers, and cut to size by a saw blade to fit into a blind bore which has been oriented and drilled into the patient's arthritic defect area. This workstation while an improvement over existing procedures is cumbersome to use and requires experience and training to use.

The present invention was designed to overcome prior art procedures and provide a simple to use allograft plug cutting assembly which accurately cuts an allograft core from an allograft condyle for use as an implant to repair a cartilage defect.

SUMMARY OF THE INVENTION

A surgical kit having component parts capable of use in the formation of an allograft implant plug from an allograft workpiece having a subchondral bone base and a cartilage cap for the repair of a cartilage defect. The kit comprising; a sizing gauge used to accurately measure the plug diameter to be cut on the workpiece, an adjustable cutter guide adapted to be fixed over the allograft workpiece to define the position of the cylindrical cut for the implant plug and a cartilage plug coring assembly with a cylindrical coring bit and arbor. The coring bit is adapted to cut a cylindrical core from the workpiece and a hammer is used to drive the cylindrical implant into the blind bore cut in the patient.

The method for use of the cutting assembly comprises the steps of:

a) marking the donor area of a condyle workpiece with a sizing gauge;

b) placing a cutter guide assembly over the sizing gauge and securing the same in a fixed position;

c) placing a core cutting device in the cutter guide assembly;

d) cutting a cartilage and bone core from the allograft workpiece and removing the bone core from the allograft workpiece; and e) trimming the cartilage and bone core to size.

It is an object of the invention to provide a surgical kit for forming a cleanly cut cylindrical implant plug with a sharply cut cartilage layer of the correct diameter size for the insertion into an excised bore in a patient to repair a cartilage defect.

It is still another object of the invention to provide a surgical kit which marks and defines the diameter of the core area to be cut.

It is also an object of the invention to provide a surgical kit allowing the scoring of the cartilage of a condyle so that the outer surface of the cartilage cap of the implant is clearly cut.

It is further an object of the invention to provide a surgical kit which can be easily used by the surgeon to create a correctly dimensioned allograft core plug.

It is yet another object of the invention to provide a surgical kit which can be easily cleaned and sterilized.

It is still another object of the invention to provide a kit to allow accurate allograft core diameter selections and lengths.

It is another object of the invention to provide apparatus which allows the core to be chamfered at one end.

It is a further object of the invention to provide a surgical kit which allows the creation of a cartilage repair plug having a cartilage layer which is not perforated, broken or cracked.

These and other objects, advantages, and novel features of the present invention will become apparent when considered with the teachings contained in the detailed disclosure along with the accompanying drawings.

BRIEF DESCRIPTION OF THE DRAWINGS

FIG. 1 is an exploded perspective view of the various components of the inventive allograft transplant plug cutting assembly;

FIG. 2 is a perspective view of the implant marking gauge shown in FIG. 1;

FIG. 3 is an enlarged side elevation view of the implant/lesion marking gauge shown in FIG. 2;

FIG. 4 is a top plan view of the distal end of the implant marking gauge of FIG. 3;

FIG. 5 is a bottom plan view of the proximal end of the implant/lesion marking gauge shown in FIG. 3;

FIG. 6 is a cross section of the implant/lesion marking gauge of FIG. 3 taken along line 6'-6';

FIG. 6A is a cross section of FIG. 3 taken along line 6'-6' when the implant marking gauge is of a solid construction;

FIG. 8 is an enlarged perspective view of the vice base member of the cutter guide assembly;

FIG. 9 is a enlarged perspective view of the adjustable arm guide assembly for the vice base member; shown in FIG. 8

FIG. 10 is an enlarged perspective view of the mallet shown in FIG. 1;

FIG. 11 is an enlarged side elevational view of the mallet shown in FIG. 10;

FIG. 12 is an enlarged front elevational view of the mallet shown in FIG. 10;

FIG. 13 is a top plan view of the mallet shown in FIG. 11;

FIG. 18 is a perspective view of the cut allograft implant plug held in a coring bit which is pushed rearward from the coring bit by a tubular push rod;

FIG. 19 is a perspective of the arbor used with the coring bit of FIG. 15;

FIG. 20 is an enlarged top plan view of the arbor shown in FIG. 19;

FIG. 21 is a side elevation view of the arbor shown in FIG. 20;

FIG. 22 is a reduced cross sectional view of the arbor of FIG. 21 taken along lines 22'-22';

FIG. 23 is a top plan view of a chamfer tool used on the implant plug;

FIG. 24 is a side elevational view of the chamfer tool shown in FIG. 23;

FIG. 25 is a side elevation view of a cartilage implant tamp;

FIG. 26 is a cross sectional view of the cartilage implant tamp of FIG. 25;

FIG. 27 is a side elevation view of the bore gauge used in measuring the depth of the defect bore;

FIG. 28 is an enlarged view of the gauge head of FIG. 27;

DESCRIPTION OF THE INVENTION

Figure 7:
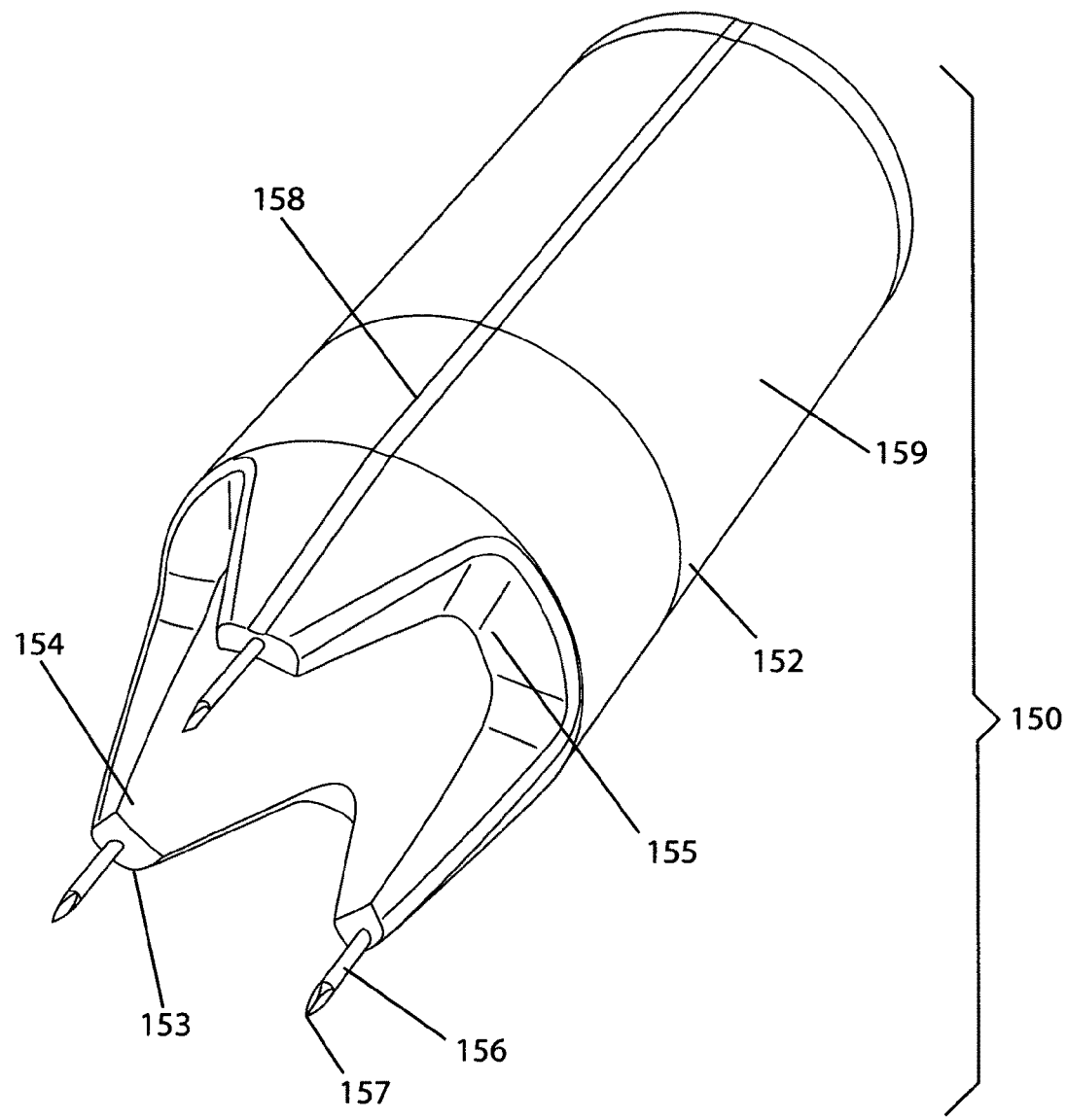
FIG. 7 is a perspective view of an alternate tube embodiment of the marking gauge.

The term "tissue" is used in the general sense herein to mean any transplantable or implantable tissue such as bone.

The terms "transplant" and "implant" are used interchangably to refer to tissue (xenogeneic or allogeneic) which may be introduced into the body of a patient to replace or supplement the structure or function of the endogenous tissue.

The terms "autologous" and "autograft" refer to tissue or cells which originate with or are derived from the recipient, whereas the terms "allogeneic" and "allograft" refer to tissue which originate with or are derived from a donor of the same species as the recipient. The terms "xenogeneic" and "xenograft" refer to tissue which originates with or is derived from a species other than that of the recipient.

The present invention is directed towards a cartilage plug cutting assembly 20 as seen with the components exploded in FIG. 1 for cutting an allograft plug 220 for use in the repair of a cartilage defect. The preferred embodiment and best mode of the invention is shown in FIGS. 1-6, 8-13 and 15-26.

In the preferred embodiment of the allograft implant cutting kit 20, a cartilage lesion/implant gauge 30 is used to mark the area on the condyle 200 and orient the articulated arm assembly 70 so that an allograft cylindrical cartilage repair plug of the correct dimension can be obtained. The lesion/implant gauge 30 as best seen in FIGS. 2-6 is placed on the surface of the condyle workpiece 200 so that the correct orientation of an implant plug corresponding to the defect bore is obtained. It will be appreciated that the gauge 30 is substantially cylindrical and can have different sized diameters ranging from 10, 15, 18, 20, 22, 25, 30 and 35 mm. Furthermore each implant cutting kit comes with a number of different sized (diameter) gauges to allow the covering of cartilage defect areas of different sizes and the marking of corresponding areas on the cartilage bone workpiece. The gauge body 32 has a solid one piece construction with cylindrical distal or front section 34, a tapered or conical middle section 35 and a larger diameter proximal or rear section 36. The material forming the gauge body 32 is preferably color coded in different colors representing the different diameters of the gauge body 32. The distal end section 34 of the gauge body 32 is formed with a plurality of extending legs 38 forming a tripod configuration and a linear sighting channel 40 is cut in the exterior surface of the body running from the proximal end of the body to the bottom of each leg 38 to form a sighting line for the surgeon as can be seen in FIG. 3. A central throughgoing bore 42 is formed in the gauge body 32 and the bore 42 widens at its proximal end in a funnel or cone shape 44 with a chamfered edge 46 which allows easy insertion of the guide drill rod only during the initial defect removal. This bore 42 is only used in the defect removal steps and is not used in the implant forming steps and the gauge body 32 can be solid without a bore as shown in FIG. 6A. The present bore construction of FIGS. 2-6 is shown simply to use the lesion defect gauge which is included in the kit for the defect removal and thus avoid the addition of another gauge in the complete cartilage repair kit. However, the solid gauge can be additionally added if desired. A cup shaped recess 43 is cut into the distal end of the body section 34.

An appropriate sized body (diameter) 32 is selected and placed in a three point stance on the condyle cartilage surface 201 and alignment marks (not shown) are drawn on the cartilage surface 201. The tripod leg structure of the body offers greater stability on the slippery condyle cartilage surface. The orientation of the tripod legs 38 assure correlation of alignment of the allograft core to the patient's defect bore. The surgeon selects an appropriately sized gauge which also determines the size of the cutter bit. It will be appreciated that a like number of cutter bits having corresponding diameters to those of the lesion gauges are also provided in the kit. The patients defect site is marked at 12 o'clock and at approximately 4 and 8 o'clock if the surgeon so chooses. The 12 o'clock position is critical. The same marking are placed on the osteochrondal core created from the allograft workpiece.

In the inventive allograft plug cutting assembly 20, a gauge 30 as seen in FIG. 2 is used to measure the external diameter of the plug or core and is positioned on the allograft workpiece that the plug or core will be taken from.

An alternative donor cutter guide member 150 as shown in FIG. 7 can be utilized. The donor cutter guide 150 has a tubular cylindrical body 152 with a distal end 153 which defines three triangular shaped legs 154 and three cutouts 155. An anchoring pin 156 is mounted in the end of each triangular shaped leg 154 for insertion into the allograft condyle surface to keep the cutter guide 150 in a fixed position during the implant core cutting. Each anchoring pin 156 has a tri-cut end point 157. The cylindrical body 152 defines a siting line 158 which is cut longitudinally in the exterior surface of the body 152 ending at the base of the anchoring pin 156. The proximal end portion of body 152 defines a knurled grip surface 159 which aids in the handling of the cutter guide.

Figure 14:
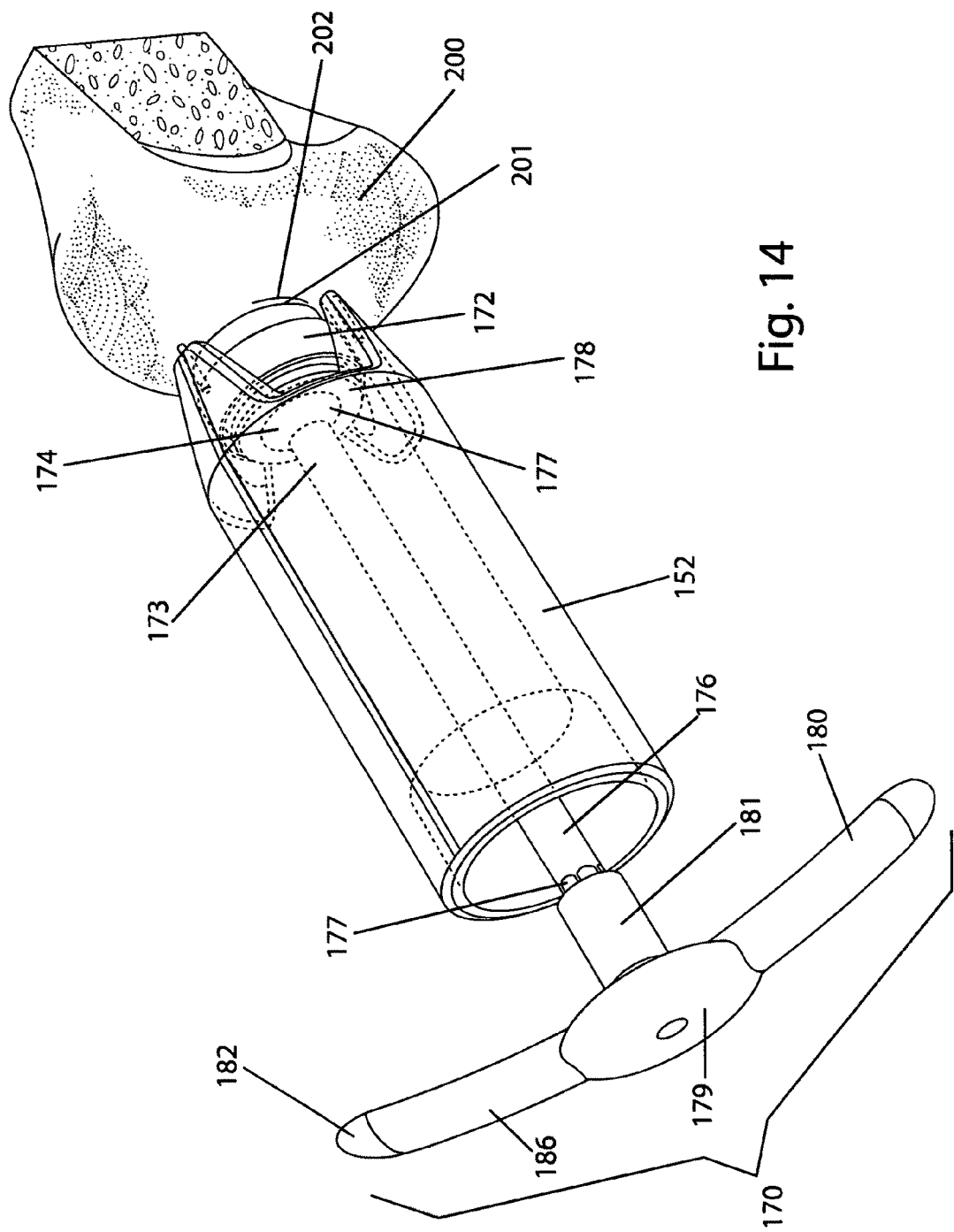
FIG. 14 is an enlarged perspective view of a T shaped handle and donor punch cutter shown mounted in the donor cutter guide showing scoring of the plug diameter on the allograft condyle.

If desired, a donor punch cutter 172 can be used to score the cartilage surfaces 201 prior to cutting the plug with the cylindrical coring bit 80. The punch cutter 172 is threadably mounted to a cannular T-handle assembly 170 as shown in FIG. 14. The punch cutter 172 has a cylindrical body 174 with a threaded collar on the proximal end and a sharpened inwardly beveled distal cutting edge. The punch cutter 172 is constructed of stainless steel. The T-handle assembly 170 for the punch cutter 172 is constructed with interchangeable tubular shafts 176, the distal end 173 being secured to a threaded stepped collar 174 which receives the threaded collar of the punch cutter 172. The proximal end of shaft 176 has a quick release socket 177 which holds the removable handle assembly 170 on the shaft 176. The handle assembly 170 has a circular impact surface 179 with an extending tubular section 181 which fits over the quick release socket 177. Handle arms 180 extend outward from the circular impact surface 179 and have curved ends 182. The top surface 186 and bottom surface 188 of the arms 180 both have a curved surface which allows the same to be easily grasped by the user. The punch cutter 172 is driven in by hand (straight and/or rotated) or hammered into the cartilage surface 201 of the patients condyle 200 to cut a clean outer diameter score for the donor transplant plug.

The T-handle assembly 170 and associated punch cutter 172 are removed from the donor cutter guide body 152 prior to mounting and the cylindrical tubular coring bit 80 (FIGS. 15-17) is placed in the bushing 79 (FIG. 9) with the cutter teeth 84 adjacent the scored area 202 of the condyle 200.

As seen in FIGS. 8 and 9, a graft workstation 50 and its associated alignment guide arm assembly 70 are used to hold the allograft cartilage bone workpiece in position so that the cutting of the implant core can be accomplished. The implant core can be held for trimming. The graft workstation 50 has a planar rectangular base 52 with feet 55 extending from its bottom surface and integral U-shaped handles 54 extending from opposite sides of the base at an angle upward from the base 52. A fixed jaw member 56 is secured to the base 52 and a moveable jaw member 58 is moveably mounted on the base 52. The moveable jaw member 58 is mounted to a screw drive having a proximal knob 61 so that turning of the knob 61 causes threaded shaft 63 to be moved with respect to screw block 59 with the distal end of shaft 63 which is mounted to the moveable jaw member 58 causing the moveable jaw member 58 to slide over the upper surface 53 of the base. As previously noted, the screw drive is threadably mounted in a screw block 59 which is secured to base 52. Each of the opposing faces of fixed jaw member 56 and movable jaw member 58 are knurled 57 to allow the allograft workpiece and/or core implant to be firmly held in a fixed position between the jaws. Both the fixed jaw member 56 and moveable jaw member 58 define aligned cutting slots 60 forming a miter so that the implant core can be trimmed with a surgical saw. (not shown) The fixed jaw member 56 defines a stepped bore 62 which receives the seating shaft 72 of the alignment guide arm assembly 70. A locking screw 64 having a handle 66 is mounted in a threaded bore which intersects stepped bore 62. The distal end of locking screw 64 is tightened to hold seating shaft 72 in a fixed position so that bushing 79 is positioned over the cartilage covered allograft bone workpiece allowing the implant plug to be correctly cut so that it will match the patients excised bore surrounding cartilage contours. The seating shaft 72 which extends from seat body 73 holds an articulated arm mechanism 74 which can be locked into position by thumb screw 76 and its associated handle 77. The distal end member 75 of the articulated arm mechanism 74 holds yoke 75 which in turn holds bushing 79. Bushing 79 is secured in the yoke 75 by thumb screw 80.

When the articulated arm assembly 70 has been oriented, the cartilage surface of the workpiece can be scored with punch cutter 172 as previously discussed or the implant plug can be cut with a coring bit 80 having the diameter necessary to have the implant plug fit the blind bore of the patients excised cartilage defect area.

Figure 15:
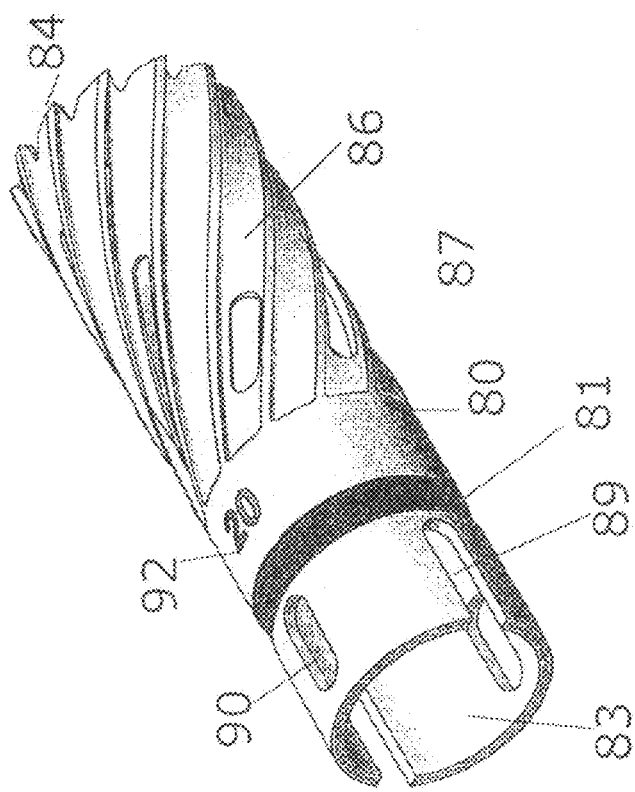
FIG. 15 is an enlarged perspective view of the cylindrical coring bit shown in FIG. 1.
Figure 17:
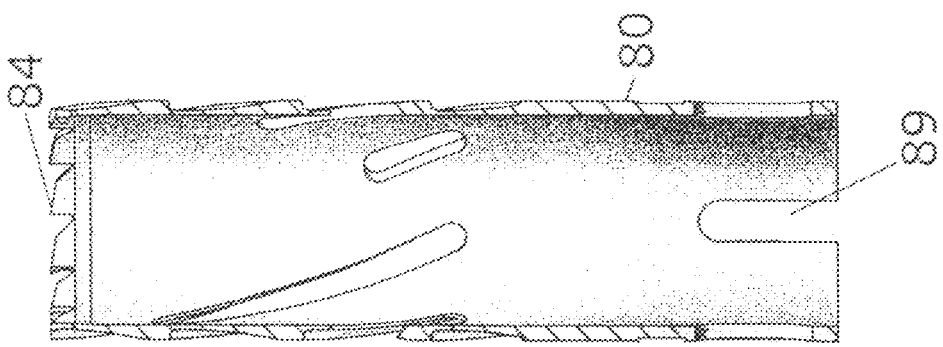
FIG. 17 is a cross sectional view of the cylindrical coring bit shown in FIG. 16 taken along line 17'-17.
Figure 16:
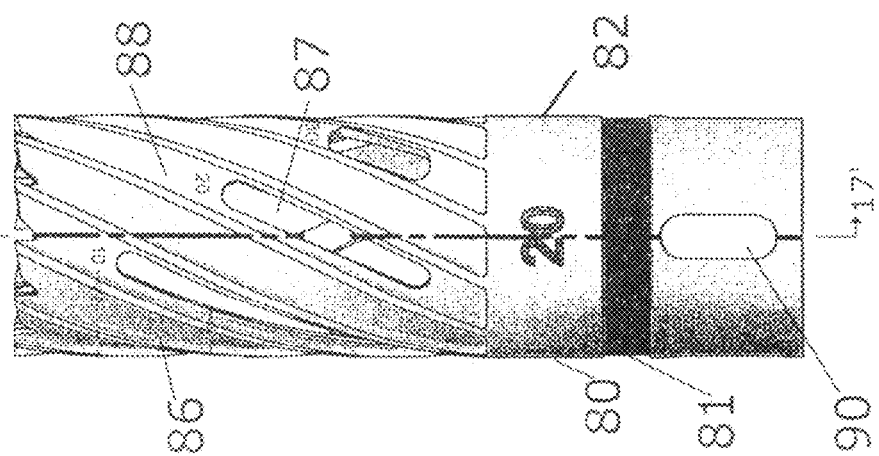
FIG. 16 is a side elevational view of the coring bit shown in FIG. 15.
Figure 29:
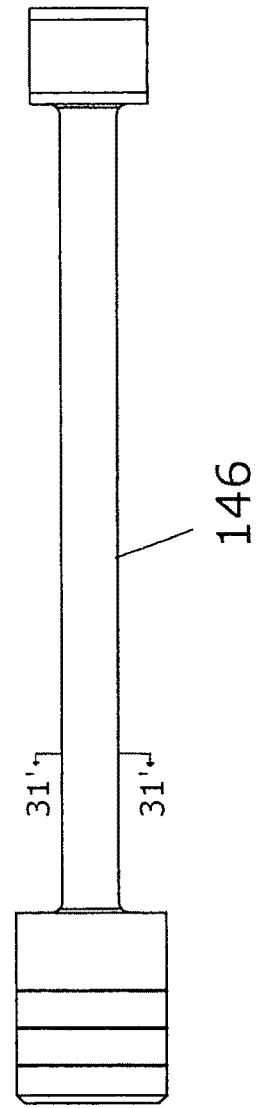
FIG. 29 is a side elevation view of the defect bore dilator.
Figure 30:
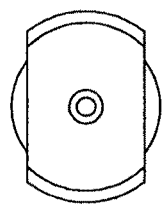
FIG. 30 is a rear end view of the distal end of the dilator shown in FIG. 29.
Figure 31:
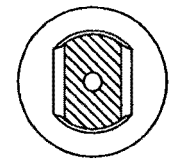
FIG. 31 is a cross sectional view taken along line 31'-31' of FIG. 29.

The coring bit 80 as best shown in FIGS. 15-17 has a cylindrical body 82 with a through going central longitudinal bore 83 having a smooth sidewall and has cutting teeth 84 formed on the distal end. The exterior surface of the body 82 defines a plurality of angled flutes 86 cut into the exterior surface with one end of each flute leading to an exterior cutting tooth surface to direct the cut allograft materials upward during cutting. The body 82 also defines oblong slots or apertures 87 which run along the base of channel 88 of alternating flutes and communicate with the through going internal bore 83 allowing for internal chip removal and providing a plug visualization and depth window. The proximal end of the body 82 defines opposing open slots 89 which act as arbor 100 engagement slots for arbor seating pins 102 as shown in FIGS. 19-22 and opposing closed slots 90 engage arbor lock mechanism 103. The coring bit body 82 has a colored band 81 which denotes the different diameters of each cylindrical coring bit body 82. The cutting bit arbor 100 shown in FIGS. 19-22 is attached by shank 104 to a drill and is driven by a standard drill (not shown) and the rotating cutting action results in the production of an allograft cartilage capped plug 220 having a cartilage surface 210 and a bone base 212 as seen in FIG. 18. A tubular centering guide 102 is used as a push stick to engage the bone base of the allograft implant plug 220 to push the plug out of the back of the coring bit 80 for trimming in the miter box of the vice work station 50 or by grasping the implant core plug with forceps and cutting the bone end with a surgical saw.

The vise work station 50 as shown in FIG. 8 as previously noted is used to hold the core or plug 220 in a fixed position for trimming. The implant plug is then trimmed by using a saw along miter slot 60 to cut the allograft plug to the desired length for placement in the bind bore which has been previously cut in the patient. The trimmed plug 220 has a cartilage cap 210 and bone base portion 212.

After trimming the length of the implant to size, the bone end of the implant is chamfered in a chamfer tool 110 as shown in FIGS. 23 and 24. The chamfer tool 110 has a body 112 in the form of a flat plate with rounded ends and defines a plurality of different diameter circular apertures 114 into which a plurality of teeth 116 protrude. The teeth have sharpened end edges 117 which cut a chamfer in the bone end 212 of the cylindrical implant 220 as the implant is rotated in the corresponding chamfer tool diameter aperture 114.

A mallet 90 as shown in FIGS. 10-13 is used to tap the implant into the bore using an impact tamp 130 as shown in FIGS. 25 and 26. The mallet 90 is preferably constructed of stainless steel has a cylindrical barrel shaped head 91 with a centrally positioned shaft 92 extending therefrom. An ergonomically shaped silicone handle 94 is secured to the shaft 92. The head 91 defines a longitudinal slot 95 and has planar end surfaces 96. Transverse angular channels 98 are positioned on opposite sides of the head with the center axis of the channels being substantially parallel and in line with the center axis of shaft 92 and perpendicular to the axis of slot 95.

A graft impactor tamp 130 is used to tamp the implant into the blind bore. The tamp 80 has a cylindrical body 132 and ranges in different sizes from 10 to 35 mm in diameter and is provided with color banding (not shown) to differentiate the different diameter sizes. The tamp body 132 defines opposing recesses 134 and 136 with one recess having a chamfered internal edge 135 and the other recess body end section having a chamfered outer edge 137.

In operation, prior to the cutting of the implant plug, a gauge 140 as shown in FIGS. 27 and 28 is used to measure the diameter of the allograft plug to be cut by using the gauge 140 to determine the depth and diameter of the blind bore which has been cut into the patient. The head 142 of the gauge with its chamfered end 143 is inserted into the blind bore of the excised cartilage defect of the patient and the cylindrical head shows the depth of the bore by its outer depth marking indicia 144 at the 12, 4 and 8 o'clock markings. If desired, the blind bore can be expanded by using a dilator 146 in the bore.

The cartilage area surface 201 is marked with a pen or other marking device around gauge 30 to determine the orientation of the plug cut. The articulated arm assembly 70 is then orientated and fixed in place so that the bushing 79 holds the gauge 30 in the correct position. If the surface is to be scored, a punch cutter 172 is threadably mounted to a cannular T-handle assembly 170 and mounted in the bushing where it engages cartilage surface 201 of the condyle and is twisted or hammered to score 202 the cartilage surface forming the outer diameter of the allograft plug The T-handle assembly 170 may be driven with a mallet 90 so that the cartilage surface 201 of the condyle 200 is cut by the punch cutter 172 leaving a clean cartilage cut for the plug 220 without cracking or shattering of the cartilage allowing the plug 220 to be cut out of the condyle 200. The associated punch cutter 172 and T-handle assembly 170 is removed from the cutter guide and the cylindrical coring bit 80 which is selected in size to correspond to the diameter of the lesion gauge 30 cuts around the circular scored cut or the marked surface 202 so that the rotating teeth 84 cut a plug core from the condyle having an associated cartilage cap 210 and subchondral bone portion 212. The result is a cleanly cut plug 220 as seen in FIG. 18.

The length of the osteochondral plug implant can be trimmed in the workstation 50 by cutting the same in the miter slot 60 or by holding in the implant core in a forceps and cutting the same with a surgical saw. The trimmed plug is removed from the coring bit and the bone end is chamfered in the chamfering tool 110. The chamfered implant is placed in the patient's defect area blind bore and tapped into place using the mallet and tamp 130 so that the cartilage surface of the implant is level with the cartilage surface of the patient surrounding the defect excision depending upon the desires of the surgeon. If the plug is the same length, the base of the plug implant is supported and the articular cartilage cap is level with the articular cartilage of the patients bone surface. If the plug is of a shorter length, the base of the plug implant is not supported but support is provided by the wall of the bore or respective cut out area as the plug is interference fit within the bore or cut out area with the cap being flush with the articular cartilage depending on the surgeon's preference. With such load bearing support the graft surface is not damaged by weight or bearing loads which can cause micromotion interfering with the graft interface producing fibrous tissue interfaces and subchondral cysts.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive.

What we claim is:
1. A surgical kit having component parts capable of use to form a cylindrical allograft implant plug for the repair of a cartilage defect from an allograft bone workpiece, said kit comprising;

a sizing gauge used to measure the implant plug diameter on the surface of said allograft bone workpiece from which a cartilage implant plug is to be cut;

an adjustable guide member adapted to be mounted over an allograft bone workpiece, said adjustable guide member comprising a vise base and a moveable arm mechanism, a yoke mounted to said arm mechanism and bushing means mounted in said yoke, said arm mechanism being provided with securing means for securing the same in a fixed positional relationship to the allograft bone;

implant plug cutting means adapted to be mounted in said adjustable guide member, said plug cutting means comprising at least one cylindrical tube with tubular body formed with cutting teeth at its distal end, said tubular body defining a plurality of spiraled flutes on the exterior surface of said body with channel between adjacent flutes, said plug cutting means being substantially open at its proximal end and arbor means removably mountable at said substantially open proximal end, and a plurality of sizing gauges, said plug cutting means further comprising a plurality of cylindrical tubes of varying diameters.

2. A surgical kit as claimed in claim 1 including a cylindrical tamp, said tamp defining circular recesses in each end with at least one recess defining a chamfered edge.

3. A surgical kit as claimed in claim 1 wherein said bushing means is a plurality of bushings of different diameters and said plug cutting means is a plurality of cylindrical tubes of different diameters with cutting teeth on their distal end.

4. A surgical kit having component parts capable of use to form a cylindrical allograft implant plug for the repair of a cartilage defect from an allograft bone workpiece having a cartilage surface, said kit comprising;

a cylindrical sizing gauge used to measure the implant plug diameter on the surface of said allograft bone workpiece from which a cartilage implant plug is to be cut;

an adjustable guide assembly adapted to hold said cylindrical sizing gauge and be mounted over said allograft bone workpiece, said adjustable guide assembly comprising a vice assembly, having a body with a fixed jaw member and a moveable jaw member mounted thereto and an adjustable arm assembly mounted to said fixed jaw member for holding said gauge and a cylindrical plug cutting means, said adjustable guide assembly being provided with securing means for securing said guide assembly in a fixed positional relationship to the allograft bone workpiece;

said plug cutting means adapted to be mounted in said adjustable guide assembly so that it has the same central axis as that of said sizing gauge, said plug cutting means comprising at least one cylindrical tube with a tubular body formed with cutting teeth at its distal end, said tubular body defining a plurality of spiraled flutes on the exterior surface of said body with a channel formed between adjacent flutes, a plurality of slots formed in said channels, each cylindrical tube being substantially open at its proximal end and arbor means removably mountable at said substantially open proximal end.

5. A surgical kit as claimed in claim 4 including a gauge used to measure the depth and diameter of a blind bore into which said implant plug is to be placed.

6. A surgical kit as claimed in claim 4 wherein said adjustable arm assembly comprises a moveable pivotable arm mechanism, a yoke mounted to said arm mechanism, a bushing mounted in said yoke and means to secure said bushing in said yoke.

* * * * *